United States Patent
Lutz et al.

(10) Patent No.: US 10,261,082 B2
(45) Date of Patent: Apr. 16, 2019

(54) FELINE LEUKEMIA VIRUS TRANS-MEMBRANE PROTEIN P15E FOR DIAGNOSIS OF FELV INFECTION

(71) Applicant: UNIVERSITAT ZURICH, Zurich (CH)

(72) Inventors: Hans Lutz, Rudlingen (CH); Eva Bonzli, Zurich (CH); Regina Hofmann-Lehmann, Rapperswil (CH)

(73) Assignee: UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 15/294,712

(22) Filed: Oct. 15, 2016

(65) Prior Publication Data

US 2017/0030910 A1    Feb. 2, 2017

Related U.S. Application Data

(63) Continuation of application No. 14/131,204, filed as application No. PCT/EP2012/063327 on Jul. 6, 2012, now abandoned.

(30) Foreign Application Priority Data

Jul. 8, 2011    (EP) .................................. 11173321

(51) Int. Cl.
G01N 33/569    (2006.01)
C07K 14/005    (2006.01)
C12N 7/00    (2006.01)

(52) U.S. Cl.
CPC ..... G01N 33/56983 (2013.01); C07K 14/005 (2013.01); C12N 7/00 (2013.01); *C12N 2740/13022* (2013.01)

(58) Field of Classification Search
None
See application file for complete search history.

(56) References Cited

U.S. PATENT DOCUMENTS 4,794,168 A * 12/1988 Elder .................. C07K 14/005
530/324
4,923,798 A *  5/1990 LeMoine ......... G01N 33/56983
422/500

FOREIGN PATENT DOCUMENTS

EP     378224    *  7/1990
EP    1754715       2/2007
WO   01/66568       9/2001

OTHER PUBLICATIONS

Langhammer et al., Immunology, 2006, 117, 229-237.*
Major et al., Vet. Res., 2010, 41:17.*
Chen et al: "Pathogenicity induced by feline leukemia virus, Rickard strain, subgroup A plasmid DNA (pFRA).", Journal of Virology, vol. 72, No. 9, Sep. 1, 1998 pp. 7048-7056.
Lutz et al. "Humoral Immune Reactivity to Feline Leukemia Virus and Associate Antigens in Cats Naturally Infect with Feline Leukemia Virus", Cancer Research, vol. 40, Oct. 1, 1980 pp. 3642-3651.

* cited by examiner

*Primary Examiner* — Nicole Kinsey White
(74) *Attorney, Agent, or Firm* — JMB Davis Ben-David

(57) ABSTRACT

The invention provides for a method for the detection of FeLV infection in a patient, wherein a sample obtained from the patient is contacted in-vitro with a recombinant trans-membrane p15E protein in a p15 (E) antibody binding step.

10 Claims, 8 Drawing Sheets
Specification includes a Sequence Listing.

Fig. 6

| SP>80% | Provirus | p45 | FL-74 | EPK211 | p15E |
|---|---|---|---|---|---|
| Provirus |  | 0.18 | 0.13 | 0.08 | 0.55 |
| p45 | 0.69 |  | 0.42 | 0.16 | 0.21 |
| FL-74 | 0.47 | 0.45 |  | 0.24 | 0.12 |
| EPK211 | 0.47 | 0.57 | 0.42 |  | 0.06 |
| p15E | 0.96 | 0.70 | 0.51 | 0.48 |  |

FELINE LEUKEMIA VIRUS TRANS-MEMBRANE PROTEIN P15E FOR DIAGNOSIS OF FELV INFECTION

CROSS REFERENCE TO RELATED APPLICATIONS

This is a Continuation of U.S. patent application Ser. No. 14/131,204, filed Jan. 7, 2014, and now abandoned, which is the US National Stage of International Patent Application No. PCT/EP2012/063327, filed Jul. 6, 2012, which claimed the benefit of European Patent Application No. 11173321.8, filed Jul. 8, 2011. The foregoing patent applications are incorporated by reference herein in their entirety.

BACKGROUND

FeLV infection is a disease of veterinary importance able to induce multifaceted clinical signs as anemia, tumors, and immunodeficiency. In spite of effective vaccines, FeLV infection is still present but differs significantly in most study populations (Levy et al., 2006, *J Am Vet Med Assoc.* 228(3): 371-6).

After infection, FeLV first replicates in the local lymph nodes or the tonsils. Infected lymphocytes transport the virus to the bone marrow, where the virus replicates at high rates and finally spreads through the whole body via the blood stream. Integration of FeLV to the cells of the bone marrow and the blood renders a cat provirus positive. A cat becomes viremic if the virus is detectable in the blood. By infection of the mucosa of the bladder and/or the epithelia of the intestine and the salivary glands, FeLV can start a new cycle of infection.

Diagnosis of FeLV mainly relies on the detection of virus or virus antigen in the plasma, serum or whole blood. The most common serological tests detect either the presence of FeLV p27 antigen by enzyme-linked immunosorbent assay (ELISA) (Lutz et al. J. Immunol. Methods 56, 209-220 (1983), Lutz et al., *Am J Vet Res.* 44(11): 2054-9), or FeLV structural antigens in the cytoplasm of infected leukocytes and platelets by immunofluorescence antibody test (IFA; Hardy et al., 1991, *J Am Vet Med Assoc.* 199(10): 1327-35; ibid. 1365-73.). Moreover, western blot analysis detects the presence of FeLV antibodies. Alternatively, non-serological diagnoses include virus isolation (Jarrett O and Ganiere J P. *Vet Rec.* 138(1): 7-11), or the polymerase chain reaction (PCR) to detect proviral (FeLV DNA)—and viral load (FeLV RNA, Hofmann-Lehmann R et al. 2001. *J Gen Virol.* 82(Pt 7): 1589-96, Herring I P et al. 2001. *Vet Ophthalmol.* 4(2): 119-26, Jackson et al., 1996. *J Vet Diagn Invest.* 8(1): 25-30. Due to the time-consuming and/or cost-intensive character of most of these methods, they are not suitable for practical and clinical use. A serological test to detect FeLV antibodies for diagnosis has not been available until now, because no evidence has been provided regarding how reliable antibody detection is for predicting FeLV infection, and which antibodies are suitable.

FeLV disease outcomes in infected cats are rather unpredictable. They were termed abortive (provirus negative), progressive (persistently p27 positive, provirus positive, FeLV RNA positive, virus isolation positive), and regressive (p27 negative, provirus positive after or without transient antigenemia). It has however been reported (Gomes-Keller M A et al. 2009. *Vet Microbiol.* 134(3-4): 208-17; Major A et al. 2010. *Vet Res.* 41(2): 17.) that cats that may remain provirus negative in the blood but seroconvert, revealing that FeLV infection has occurred. Disease detection in these cats is detectable solely by a laborious and expensive serological procedure (immunofluorescence assay to feline oncornavirus-associated cell membrane antigen, 'FOCMA-test').

Until now, detection of antibodies to FeLV had limited significance as a means of diagnosis in veterinary practice, due to the widespread existence of endogenous FeLV (enFeLV) in cat populations. Because enFeLV is not tolerated by the immune system, antibodies are elicited (Langhammer et al. 2006. *Immunology.* 117(2): 229-37) which are undistinguishable from antibodies to exogenous FeLV. Only PCR is able to distinguish between endogenous and exogenous FeLV. Thus, FeLV antibodies were so far not considered to be useful as a diagnostic parameter. Moreover, several studies failed to detect a sufficient antibody response against various epitopes of FeLV. Fontenot and co-workers (*J Clin Microbiol.* (1992) 30(7): 1885-90) have analyzed the reactivity of a predicted FeLV transmembrane immunodominant domain (Imd-TM peptide, 26 amino acids long), and investigated its potential as a diagnostic reagent in serology. In the cited study, the peptide displays only negligible levels of reactivity using sera from FeLV-infected cats, which leads the authors to conclude that the Imd-TM peptide is not useful for FeLV diagnosis. Langhammer et al. (*Immunology.* 2006; 117(2): 229-37) recombinantly produced a FeLV p15E polypeptide covering the ectodomain (AA 476-583) and showed that cats infected with FeLV developed antibodies against p15E, although the reactions in ELISA were low. Epitope mapping revealed a variety of epitopes recognized by sera from FeLV-infected animals, including epitopes detected by sera from p15E-immunized cats, but the response in the infected animals was weaker than in vaccinated animals. The study concluded that natural FeLV infection results in a weak induction of antibodies specific for p15E, and a low induction of neutralizing antibodies.

SUMMARY

The objective of the present invention, in some embodiments, is to provide safe and economic methods and means for the detection of FeLV infection in cats, particularly for the diagnosis of latent transmissible FeLV infection in the absence of p27-positive viremia. This objective is attained by the subject matter of the independent claims.

"FeLV infection" as used herein refers to the presence and replication of exogenous FeLV, as opposed to the presence of endogenous FeLV sequences in the germline.

The basis of certain embodiments of the present invention is the surprising observation that binding of antibodies to recombinant transmembrane protein p15E that includes its N-terminal amino acid sequence, is a tool of significant diagnostic power for the detection of past and present FeLV infection even in cases where infection cannot be detected by conventional methods such as p27 detection by ELISA. The invention is the outcome of a study on the utility of four FeLV antigens for serology as an alternative approach in FeLV diagnosis: a recombinant env-gene product (p45), whole virus, a short peptide from the FeLV TM C-region, and recombinant p15E comprising the full cytoplasmic sequence. Sera from experimentally infected and immunized cats, as well as from a field study, were examined by ELISA. From each sample, proviral-, p27-, and immunization status was known.

SHORT DESCRIPTION OF THE FIGURES

Figure 3:
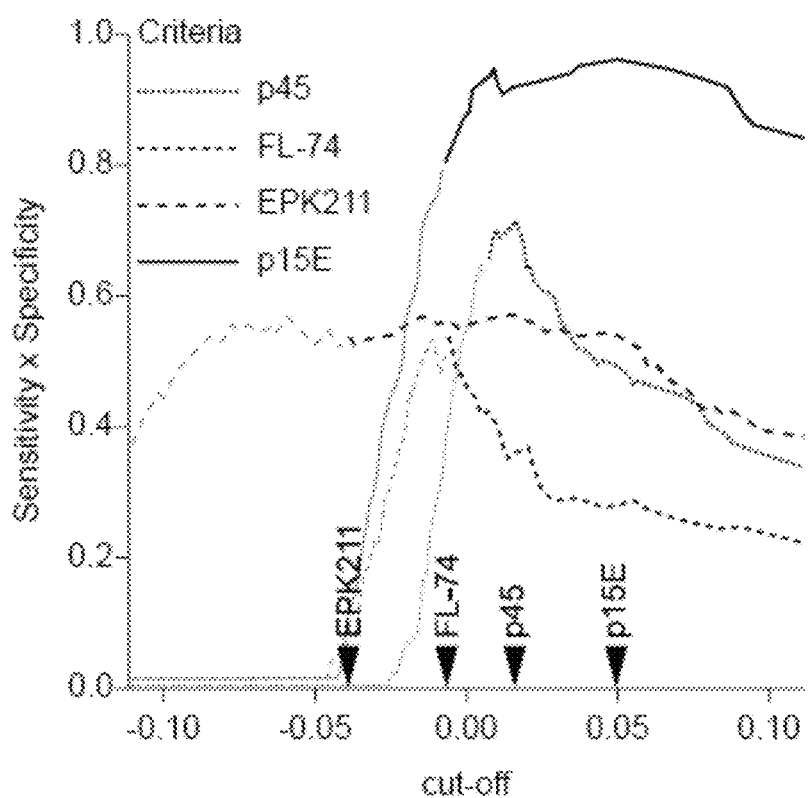

FIG. 3 shows the determination of the optimal cutoff value for experimentally infected cats with the sensitivity x specificity (y-axis) plotted against the cutoff (x-axis). Dark lines represent specificities ≥80%. The arrows indicate the cutoff points.

Figure 4:
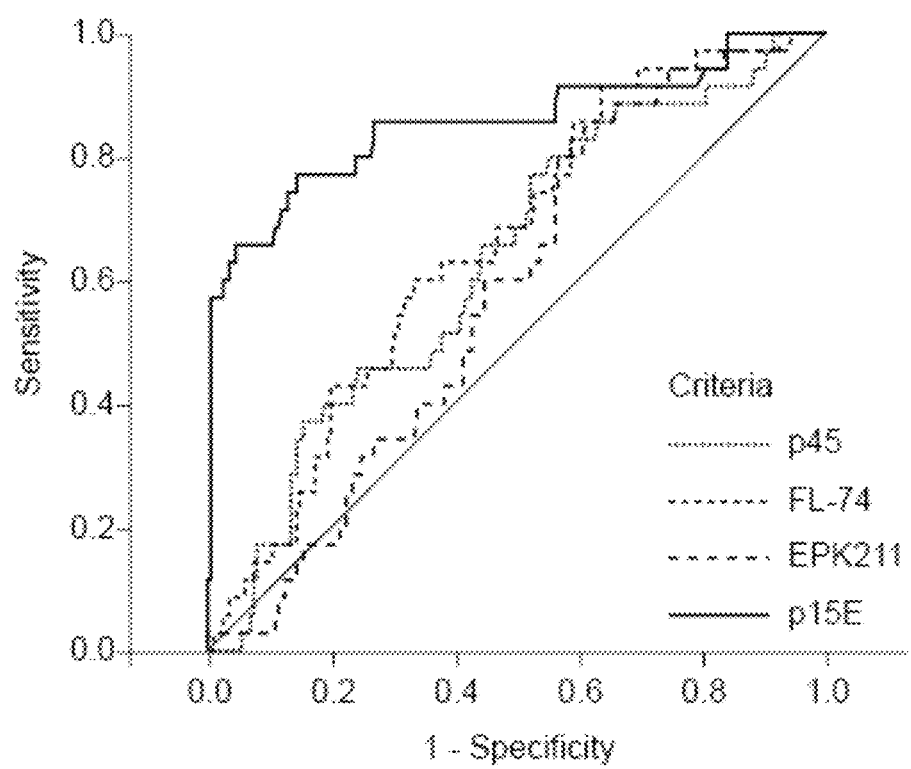

FIG. 4 shows an empirical receiver operating characteristic (ROC) curve of provirus for field study cats. The true positive rate (sensitivity, y axis) is plotted against the false positive rate (1-specificity, x-axis) at various cutoffs.

Figure 5:
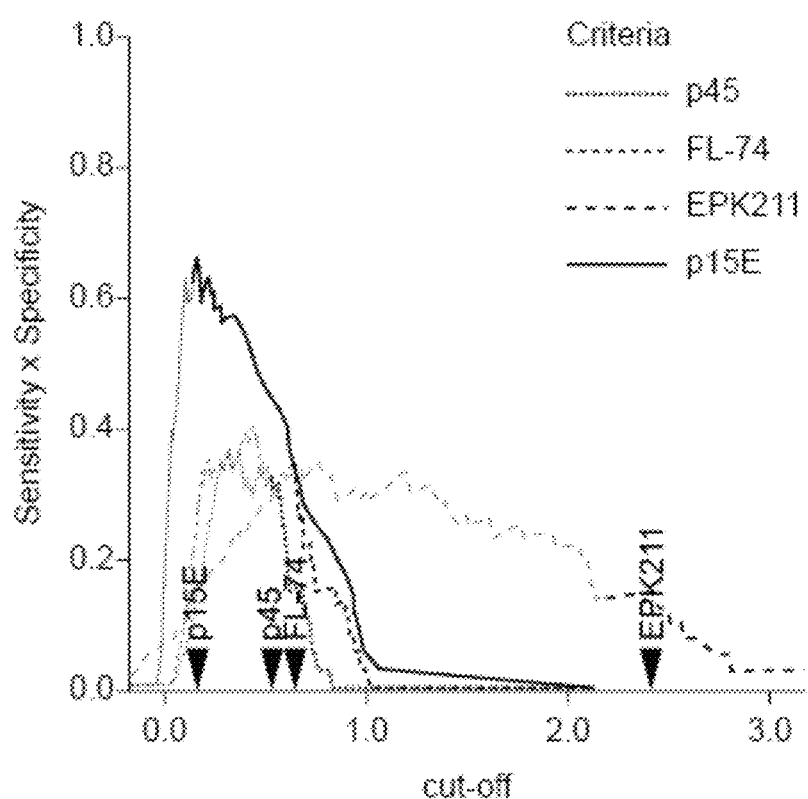

FIG. 5 shows the determination of the optimal cutoff value for experimentally infected cats with the sensitivity x specificity (y-axis) plotted against the cutoff (x-axis).

FIG. 6 shows the extent of agreement between different methods for determination (Cohen's κ-(=kappa)-values.

Figure 7:
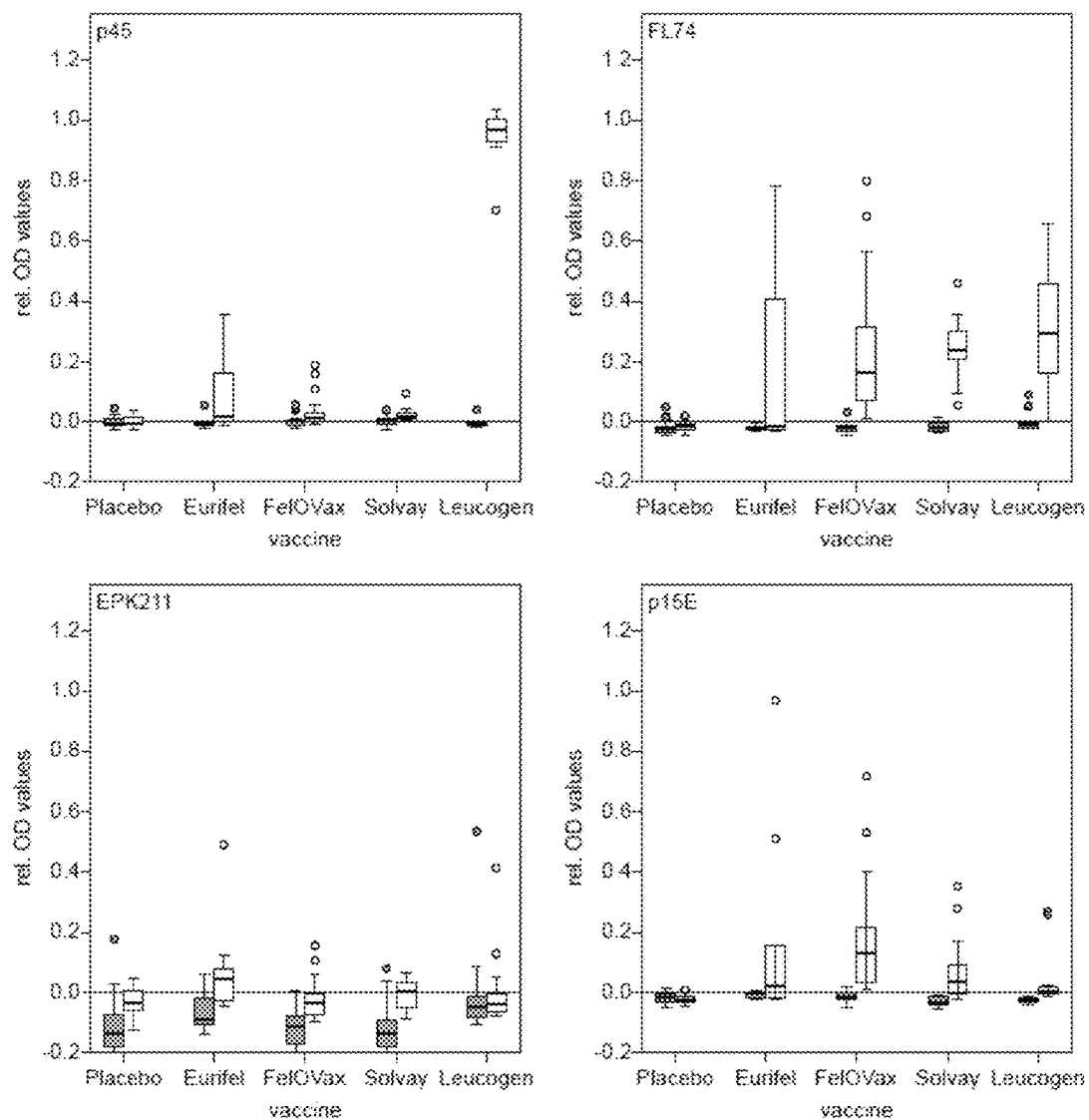

FIG. 7 shows p15E reactivity in experimentally vaccinated cats, with the y-axis representing the relative OD values and x-axis the different vaccines used in the study. The gray bars: 8 weeks old SPF-cats before vaccination, white bars: same kittens after 2 vaccinations, before challenge experiments.

Figure 8:
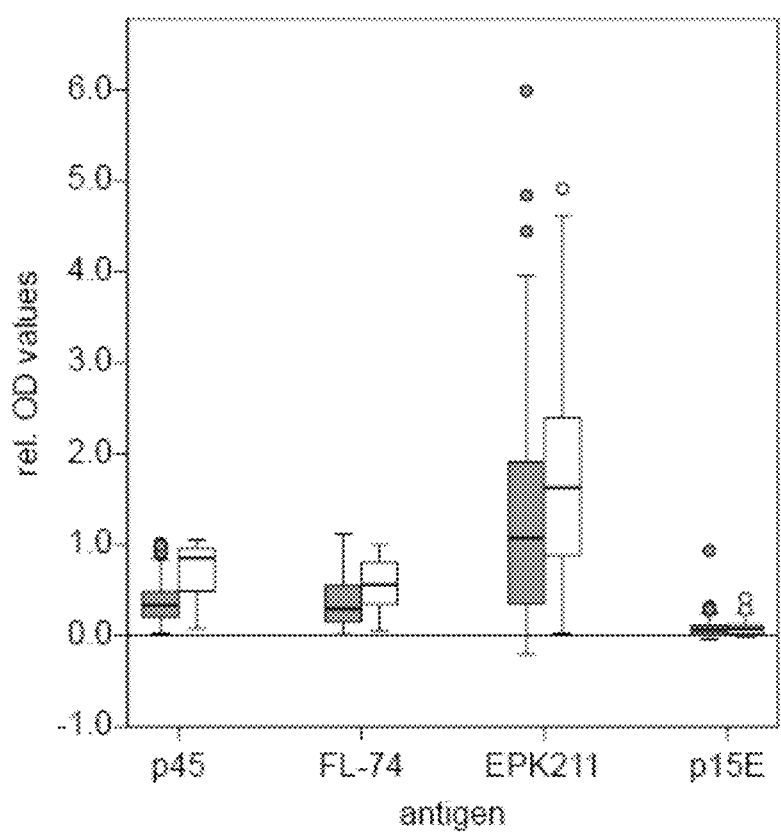

FIG. 8 shows reactivity to the 4 different antigen preparations in vaccinated field study cats, with the y-axis representing the relative OD values and x-axis the antigens.

BRIEF DESCRIPTION OF THE DESCRIBED SEQUENCES

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_303_6001_seq.txt, created Oct. 15, 2016, about 3 KB, which is incorporated by reference herein.

DETAILED DESCRIPTION

According a first aspect of the invention, a method for the detection of FeLV infection in a patient is provided, wherein a sample obtained from said patient is contacted in-vitro with a recombinant transmembrane protein p15E or fragment thereof including the N-terminal amino acid sequence of the cytoplasmic region of p15E, and the presence of antibodies contained in the sample that are able to bind to the recombinant p15E protein is detected. This step is referred to as the p15 antibody detection step.

In another aspect of the invention, a method for the detection of FeLV infection in a patient is provided, wherein a sample obtained from said patient is contacted in-vitro with a protein comprising the amino acid sequence of SEQ ID 001, or a sequence at least 90% identical to SEQ ID 001, and the presence of antibodies contained in the sample that are able to bind to the recombinant p15E protein is detected.

The term "recombinant" in the context of the present invention means that the protein is produced synthetically, for example either (a) by expression in a host cell of a gene encoding the sequence of p15E transmembrane protein including the N-terminal amino acid sequence of the cytoplasmatic region of p15E; or (b) in a cell-free system, for example by solid phase synthesis of individual amino acids.

The patient is a host susceptible to FeLV infection, for example a domestic cat (*Felis catus*) an Iberian Lynx (*Lynx pardinus*) or a European wild cat (*Felis silvestris* silvestris). The sample is any patient sample that may contain antibodies. The most preferred sample is a whole blood sample or a serum sample.

According to a preferred aspect of the invention, the recombinant protein comprises or consists essentially of the amino acid sequence of SEQ ID 001 (amino acids 446-642 of FeLV-A; GenBank: AAA93093.1), or a sequence at least 90%, 91%, 92%, 93%, 94%, 95%, 96%, 97%, 98% or 99% identical to SEQ ID 001.

Identity in the context of the present invention is a single quantitative parameter representing the result of a sequence comparison position by position. Methods of sequence comparison are known in the art; the BLAST algorithm available publicly is an example.

After contacting the sample and the recombinant transmembrane protein, the binding of antibodies to the recombinant transmembrane protein is detected. Such detection of antibody binding may be effected directly, for example by measurement of the physical properties of a surface to which one of the binding partners, preferably the recombinant protein, is attached. Examples of such methods are quartz microbalance or surface plasmon (BIACORE) experiments.

Alternatively, the presence of antibodies against p15E may be detected indirectly, for example by Western-Blot or ELISA-type methods, wherein a detection antibody or ligand specific for the constant portion of a gamma immunoglobulin of the patient species is employed, and the binding of the detection antibody is detected, for example by labelling the detection antibody. Preferred labels are chromogenic enzymes, which convert a substrate into a product and the rate or quantity of product formation is detectable by spectrometry. An example is horseradish peroxidase. Another type of preferred label are luminescent proteins (e.g. luciferase) or fluorescent proteins (e.g. GFP), or fluorescent or phosphorescent dyes.

According to one embodiment, the method for detection of FeLV infection comprises a step whereby the presence of FeLV p27 protein in the sample is detected in addition to detecting the presence of antibodies binding to recombinant p15 including its N-terminal sequence.

Detection of p27 may be achieved by contacting the sample with an antibody to p27 as a homogeneous or heterogeneous assay. Antibodies reactive to p27 may be attached to a surface and binding of p27 may be measured directly, as outlined above, by surface plasmon resonance or equivalent technologies. Likewise, an antibody to p27 might be used to bind p27 to a surface, and bound p27 might be measured by a second antibody having a detectable label attached to it.

In one embodiment, the method of the invention comprises detecting p27, and binding of antibodies to the transmembrane p15E protein combined with presence of p27 protein in said sample indicates FeLV viremia, while binding of antibodies to the transmembrane p15E protein and absence of said p27 protein in the sample indicates immunity to FeLV.

Detection of p27 may be performed as a step prior to contacting the sample with recombinant p15E protein. Detection of p27 protein is an indicator of acute FeLV viremia in the patient, thus obliterating the need for further differential analysis by contacting with p15E. If however the sample proves negative for p27, the sample will be contacted with p15E in order to establish whether the patient had been exposed to FeLV in the past and may be latently infective. Alternatively, p27 and p15E detection may be combined to give a workflow no more complex than detection of either factor individually. Depending on detection reaction conditions it may be preferable to detect p27 after p15E.

Detection of FeLV p27 can be achieved for example by antibodies or ligands specific for p27, which, as outlined above, may be labelled. In an embodiment where detection of p27 and detection of p15E is effected simultaneously, the labels of antibodies to the two antigens must be different.

Likewise, according to another preferred embodiment, the presence of antibodies against p45 may be detected in addition to antibodies against p15E transmembrane protein, and optionally to presence of p27. The presence of antibodies against p45 may be achieved by similar means as those employed for detecting the presence of antibodies against p15E.

The advantage of detecting antibodies against p45 is to detect patients having undergone previous vaccination against FeLV, as p45 is an antigen common to all commercial vaccines.

The method according to the first aspect of the invention does not necessarily have to be practiced as a two-phase system, in which one of the binding partners is attached to a surface in order to detect binding of the other partner. Although such surface-liquid systems currently dominate the commercial market due to their ease of operation, the ubiquity of ELISA readers and the availability of reagents, homogeneous phase detection systems are known in the art that similarly can reliably indicate the binding of an antibody to a ligand. One example of a homogeneous phase proximity detection system is the Alpha Screen technology (Perkin Elmer), whereby a light-induced singlet oxygen species generates chemoluminescence in a nearby partner.

According to another aspect of the invention, an isolated recombinant protein having the amino acid sequence of SEQ ID 001, or in various embodiments a sequence at least 90%, 95%, 96%, 97%, 98% or 99% identical to SEQ ID 001 is provided, particularly for use in detecting FeLV virus or diagnosing FeLV infection in a patient.

```
                                                 SEQ ID 001
episl tvalmlgglt vggiaagvgt gtkalletaq frqlqmamht diqaleesis alekslts1s evvlqnrrgl dilflqeggl caalkeeccf yadhtglvrd nmaklrerlk qrqqlfdsqq gwfegwfnrs pwfttlissi mgpllillli llfgpcilnr lvqfvkdris vvqaliltqq yqqikqydpd rp
```

According to one embodiment, the recombinant protein having the amino acid sequence of SEQ ID 001, or in other embodiments a sequence at least 90%, 91%, 92%, 93%, 94%, 95%, 96%, 97%, 98% or 99% identical to SEQ ID 001, is attached to a surface. In a more preferred embodiment, this surface is the surface of a microtiter plate cavity, for example as part of an ELISA Kit, the surface of a lab-on-a-chip device or the surface of a quartz microbalance or a plasmon resonance chip. Similarly, it may be a nitrocellulose membrane or a glass fibre membrane.

According to another aspect of the invention, one or more of the surfaces defined above are comprised in a kit for serological detection of FeLV. In a preferred embodiment, this kit further comprises anti-cat immunoglobulin antibodies which are labelled. In more preferred embodiment the label comprises one or more labels from the group comprising chromogenic enzyme, luminescent or fluorescent protein or dye. In a most preferred embodiment the kit further comprises a ligand for the serological detection of p27 protein.

Suitable ligands according to the first aspect of the invention may also be developed by evolutive methods such as phage display, ribosome display or SELEX, wherein polypeptides or oligonucleotides are selected according to their binding affinity to a target of interest. Additionally, higher affinity inhibitors may be identified by reiterative rounds of evolution and selection of the amino acid sequence or nucleotide sequence.

The aim of the study underlying the present invention was to analyze the potential of different FeLV components as diagnostic agents in serology, to discriminate between uninfected and infected cats, and to evaluate the antibody levels of vaccinated cats. As a proof of principle, experimentally infected cats were tested. It could be demonstrated that as regards diagnostic potential, the best test antigen is the recombinant FeLV transmembrane (TM) protein p15E with a cutoff at OD=0.0495 with a diagnostic sensitivity of 95.7% and a specificity of 100%, but EPK211, FL-74 and p45 were not suitable. The cutoff value for p15E in field cats was at determined at OD=0.1625, with a diagnostic sensitivity of 77.1% and a specificity of 85.6%. Nearly all SPF sera tested on p15E did not have antibodies to enFeLV, but we must not exclude the possibility that certain breeds may have increased levels of antibodies to enFeLV. Nearly all cats seroconverted after contact with FeLV, and we can state that the probability that a cat is infected with FeLV is high in p27 negative but p15E positive cats. However, p15E is not able to discriminate between viremic and immune cats, indicating that p27 is further needed in diagnostics to detect viremia.

In order to assign cats to vaccination, it would be useful to test not only for FeLV antigen but also FeLV antibodies to obtain information about a potential immunity of the animal, which might render a vaccination needless. Certain vaccines, including feline leukemia virus or rabies vaccine, as well as vaccination procedures, suggest a relationship to the feline injected site-associated sarcoma (FISAS), which is a malignant disease characterized by the formation of local aggressive sarcomas with invasive behavior, and the probability of metastasing in 25-70% of all cases. FISAS is reported to have an incidence of only 1-10 per 10,000 cats.

An antibody test should not only detect immune animals but also cats that never had contact to FeLV, and must not detect antibodies to endogenous FeLV in order to be clinically useful to the practicing veterinarian. FeLV naïve animals are candidates for vaccination to avoid later infection by FeLV. The veterinarian will have to choose whether more emphasis is to be placed on detection of the immune cats, to avoid a further vaccination with the associated risk of a FISAS, or on detection of the uninfected cats for subsequent vaccination.

A cat with a p15E OD value over the cutoff is considered immune (if p27 ELISA is negative), a cat with OD value under the cutoff is considered to be naïve and susceptible to FeLV, and should be vaccinated. Vaccinated cats, which are over the cutoff are considered immune due to infection, and are not vaccinated; these cats are not at risk of being infected by FeLV. A vaccinated cat which is under the cutoff is vaccinated again, because it is considered susceptible to FeLV. In locations where almost all cats are immunized with Leucogen (such as in the field study related to herein: 98%)

veterinarians might test a p15E negative cat with p45 ELISA to be sure that it is vaccinated, to exclude the (small) risk of a FISAS with vaccination.

p15E can be used to differentiate infected from uninfected animals, but this antigen is not useful to clearly detect vaccination, because most of the vaccinated cats have antibody values that are lower than the cutoff calculated for p15E ELISA. Thus, p15E seems to be a read-out for infection rather than vaccination, consistent with previous findings (Lutz H et al. 1980. *Cancer Res.* 40 (10): 3642-51.)

Significant differences between the four antigens, and between experimentally infected cats and field study cats, were observed in the study underlying this invention. The most striking differences are, first, that p15E is by far the most potent diagnostic agent compared to all other antigens, and this is true in experimentally infected cats as well as in the field study cats. Second, the test specificity of p15E in experimentally infected cats is better than in field study cats, possibly due to the samples from experimentally infected cats being taken at specific and defined time points, in contrast to field study cats. Field cats often have an unknown prehistory, undefined ages, and undefined time points of sample taking. Furthermore it is not known how many times the field study cats were infected by FeLV, by different FeLV subtypes, or by other viruses, especially if they are foundlings, contributing to an explanation of the different test specificities. These factors might result in a less defined outcome of the cat's immune state, and to elevation of cutoff values and kappa values of the field data compared to experimental data.

In the study underlying this invention the reactivity of sera from SPF cats, experimentally infected cats, and immunized cats to four FeLV antigens, namely a recombinant env-gene product, whole virus, a 15 amino acid long peptide from the FeLV transmembrane protein, and recombinant p15E were systematically evaluated. With indirect ELISA, evidence was sought whether a cat had had contact with FeLV or not as an alternative approach for diagnosis of FeLV infection. Based on the p15E results presented here, it is concluded that serological results represent a valuable support in evaluating the infection state of a cat, at least partially replacing PCR.

EXAMPLES

Materials and Methods

Indirect enzyme-linked immunosorbent assays (ELISA) were developed for assessing their ability to serve in FeLV diagnosis. Thus, a short peptide derived from the FeLV transmembrane, a recombinant env-gene product (p45), whole FeLV antigen, and recombinant p15E were used as antigens. Sera from experimentally infected and vaccinated cats as well as field sera were examined for their reactivity to the antigens.

Antigens for ELISA p45: The non-glycosylated recombinant variant of gp70 surface unit (vaccinal antigen) of the envelope glycoprotein (Jarrett O and Ganiere J P. 1996. *Vet Rec.* 138(1): 7-11.) of FeLV-A. The antigenic suspension (Leucogen®, Virbac Schweiz AG, Glattbrugg, Switzerland) was adjuvanted with 0.1 ml of a 3% aluminium hydroxide gel and with 10 µg purified extract of *Quillaja saponaria*.

Whole virus: Whole virus originated from FL-74 cells. This lymphoblast FOCMA (Oncovirus-Associated Cell Membrane Antigen) cell line was chronically infected with FeLVABc (Jarrett et al. 1973. *J Gen Virol.* 20(2): 169-75.). Virus was sucrose gradient purified.

EPK211: This synthetic 15 amino acid peptide (Ac-GWFEGWFNRSPWFTT-NH$_2$) (amino acids 126 to 140 of SEQ ID NO: 1) mimics a part of the FeLV carboxy-terminal region of p15E. It was synthesized by solid-phase peptide synthesis and purified by analytical high-pressure liquid chromatography (purity>85%).

p15E: To produce the recombinant transmembrane part (TM) of the envelope glycoprotein of FeLV, the DNA sequence encoding amino acids 446-642 of FeLV-A (GenBank: AAA93093.1) was cloned into the pCRII Topo-vector (Invitrogen, Luzern Switzerland) and expressed in *Escherichia coli* (*E. coli*) Top10 cells. Fusion protein containing p15E was purified by affinity chromatography. Protein to be used for ELISA was dialyzed against 7.5 mM Tris-Cl buffer pH 8.0. The product was verified with western blot analysis. Presence of *E. coli* residuals in p15E was determined by ELISA using three different anti-*E. coli* sera (see FIG. 1) from 3 rabbits immunized against *E. coli* components (sera 1, 2 and 3). The results showed that hardly any *E. Coli* components were present in the purified p15(E) preparation.

Sera and Plasma Samples

Sera and plasma of different vaccine studies were employed to test for antibodies to the four antigens. The samples from the first study (n/group=9) are: Group 1—unvaccinated control animals. Group 2—vaccinated with EURIFEL® FeLV vaccine (new name: PUREVAX® FeLV vaccine; Merial, Lyon, France). EURIFEL® FeLV vaccine is a non-adjuvanted canarypox-vectored live vaccine (ALVAC) containing FeLV-A env, gag and part of pol. Group 3—vaccinated with FEL-O-VAX® FeLV vaccine LV-K IV (Fort Dodge, Iowa, USA), which is a polyvalent killed whole virus FeLV vaccine. Vaccines were injected twice subcutaneously. Four weeks after the second vaccination, each cat was challenged with FeLV-A/Glasgow-1 (Jarrett et al. 1996. *J Gen Virol.* 20(2): 169-75.).

The samples from the second study (n/group=14) done in 1997 are: Group 1—unvaccinated control group. Group 2—vaccinated with FEVAXYN® FeLV vaccine (Solvay Animal Health, Inc., Mendota Heights, Minn., USA), which consists of inactivated (or killed) antigen. Group 3—vaccinated with FEL-O-VAX® FeLV vaccine LV-K IV, and group 4 received LEUCOGEN® FeLV vaccine. Vaccines were injected twice subcutaneously. Four weeks after the second vaccination, each cat was challenged with FeLV-A/Glasgow-1. Blood was collected prior to and on the day of challenge exposure in both studies. Thereafter, samples were collected weekly until week 15. Furthermore, we used plasma from unvaccinated control groups from week 8 or 10 post challenge (n=47). For longitudinal effects on antibodies, we used the sera from the unvaccinated but challenged control groups. We used also plasma from young SPF cats (n=90), adult blood donor (SPF) cats (n=20), and for longitudinal effects we tested a negative control group (n=4) from a study consisting of cats that stayed unchallenged during 22 weeks. To test the reactivities of vaccinated cats, we used all groups from the vaccine studies and tested cats prior to vaccination and after vaccination/before challenge with FeLV-A.

Sera from privately owned cats (n=294) were also used, collected from April 2004 until January 2005 by M. A. Gomes-Keller (2006. *J Clin Microbiol.* 44(3): 916-22.). Information about the vaccination state of the cats was obtained from the veterinarians who collected the blood samples.

For all sera tested, provirus and p27 results were available. Field sera are summarized in Table 1.

TABLE 1

Overview of field study cats

| provirus | – | – | + | + | + | + |
|---|---|---|---|---|---|---|
| p27 | – | – | – | – | + | + |
| vaccine | – | + | – | + | – | + |
| # | 201 | 50 | 9 | 5 | 26 | 3 |

Enzyme-Linked Immunosorbent Assay

ELISA was based on published methods (Engvall E and Perlmann P. 1972. *J Immunol.* 109(1): 129-35, Voller et al. 1976, *Bull World Health Organ.* 53(1): 55-65.) Anti-FeLV p45 and anti-FeLV whole virus ('FL-74') antibodies were measured by ELISA as previously described (Lutz H et al. 1980. *Cancer Res.* 40(10): 3642-51, Lehmann R et al. 1991. *J Am Vet Med Assoc.* 199(10): 1446-52.). P45 and whole virus were used at final concentrations of 100 ng/well. For EPK211 and p15E were used at a final concentration of 25 ng/well with 0.005% SDS. Plasma and sera were diluted 1:200. An affiniPure goat α cat IgG (H+L) peroxidase-conjugated secondary antibody (Milan Analytica AG, Rheinfelden, Switzerland) was used at a dilution of 1:3000. ELISA plates were evaluated with a spectrophotometer (Spectramax plus 384, Molecular Devices, CA, USA) to measure optical density (OD) values with an absorbance at 415 nm. Positive and negative control sera were used as internal standards to assure comparability between runs.

P15E purity was tested using three different rabbit sera containing antibodies against specific epitopes of *E. coli*. ELISA was performed as above with an affiniPure goat α rabbit IgG (H+L) peroxidase-conjugated secondary antibody (Milan Analytica).

Data Analysis and Statistics

ELISA OD values were standardized: (OD value (sample)-OD value (negative control))/(OD value (positive control)-OD value (negative control)).

Software package NCSS® 2007 statistics software, Version 07.1.20 (LLC Kaysville, Utah, USA) and PASW® statistics software version 18.0.2 (Polar Engineering and Consulting, Nikiski, USA) were used for the receiver operating characteristic (ROC) analyses, and WIN EPISCOPE 2.0® epidemiology software (Borland International Inc.) for calculation of the kappa values. To compare the differences in the mean values between the adult SPF cats and the young SPF cats, one-way ANOVA and Welch/Brown-Forsythe test was used.

Results:

In summary, p45, whole virus, and the peptide were found to be inappropriate as antigenic agents. p15E displayed a diagnostic sensitivity of 95.7% and specificity of 100% using sera from experimentally infected cats. Using the field study sera and a different cutoff, p15E versus provirus PCR showed a diagnostic sensitivity of 77.1% and a specificity of 85.6%.

Vaccinated cats displayed only low antibody levels to p15E indicating that anti p15E antibodies are rather a sign for infection than for vaccination.

Purity of recombinant p15E.

Figure 1:
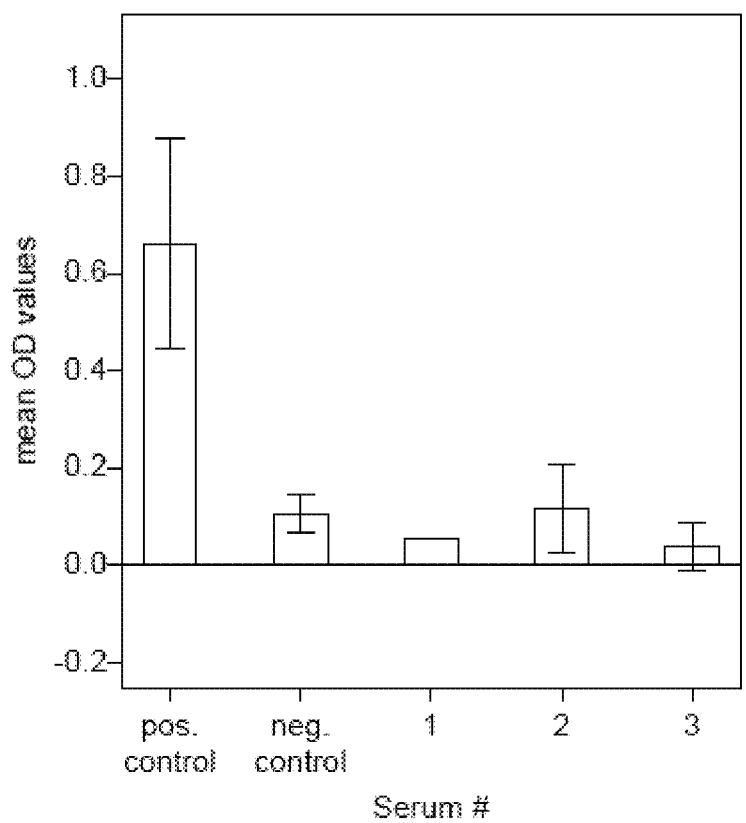
FIG. 1 shows the absence of immunogenic contaminants in recombinant p15E preparations by ELISA, plotting serum type (x-axis) against mean O.D. (y-axis).

The purity of p15E produced in *E. coli* cells was tested by ELISA on wells coated with recombinant p15E using three different sera from rabbits immunized with *E. coli* antigens. We measured the level of antibodies directed to residual *E. coli* components (FIG. 1). The OD was maximally 0.117 (serum 2) which corresponds to the negative control (OD=0.106). The other two *E. coli* sera exhibited even lower OD values. All cutoff rates correspond to raw data as derived from the experiments as described above. The person skilled in the art is able to assign cutoff rates to data derived with similar methods, which will lead to different raw OD data.

Antibody Levels in Experimentally Infected Cats.

Experimentally infected cats were compared with the field study cats by displaying them in a receiver operating curve (ROC), a plot of the true positive rate (sensitivity) against the false positive rate (1-specificity), to evaluate and compare the diagnostic utility of the different FeLV antigens.

Figure 2:
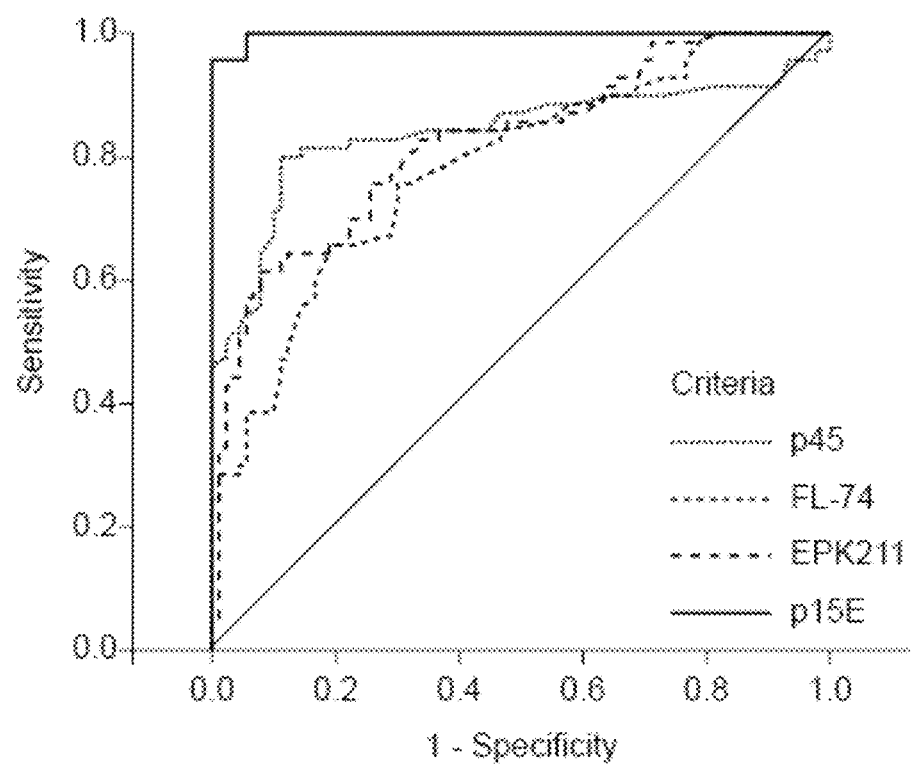
FIG. 2 shows an empiric receiver operating characteristic (ROC) curve of provirus for experimentally infected cats including SPF cats and provirus positive (p27 positive and p27 negative cats). The true positive rate (sensitivity, y-axis) is plotted against the false positive rate (1-specificity, x-axis) at various cutoffs.

In ROC analyses, cutoff points that discriminate uninfected, provirus negative, specific pathogen free (SPF) cats from infected, provirus positive (seroconverted) cats were chosen that result in optimal test specificity and sensitivity. Evaluation of experimentally infected cats represented a proof of principle. Using provirus as gold standard, the ROC curve of all antigens is represented in FIG. 2. As a rule, the optimal cutoff was defined as specificity≥80% and sensitivity x specificity as maximum (FIG. 3). Antigen p15E exhibited an excellent curve (FIG. 2), following the left-hand border and the top border of the ROC space. A cutoff of OD=0.0495 was selected, which represented the best tradeoff between sensitivity (95.7%) and specificity (100%). The optimal cutoff (−0.039) for EPK211 displayed a sensitivity of 65.7% and specificity of 81.1%, whereas p45 (cutoff 0.016) revealed a sensitivity of 80% and specificity of 88.9%. Whole virus displayed a sensitivity of 65.7% and specificity of 81.1% with a cutoff of −0.007.

Sera from 20 adult blood donor cats (SPF) of different ages, most of them exceeding 6 years, were also tested. They were not included in the proof of principle study to have a uniform data set of young SPF cats. These 20 animals were also tested on all four antigens (data not shown). Briefly, differences in mean values for all four antigen of p≤0.01 were observed, with the tendency that OD values of adult animals were more scattered and elevated compared to values of young SPF cats, indicating that the age is important in this antibody test.

Longitudinal effects on antibodies from SPF cats and challenged control group cats were also studied. SPF sera stayed low during 22 weeks, and sera from challenged cats (immune and viremic) were elevated after 4 weeks post infection and stayed at high levels (data not shown).

Cohen's κ (kappa) values, which represent a chance corrected measure of agreement between two sets of categorized data, revealed an almost perfect level of agreement (κ=0.96) between p15E and provirus (FIG. 6). The agreements between provirus and p45, whole virus 'FL-74', and EPK211 showed lower levels ranging between 0.47 and 0.70. Agreement between pairs of antigens showed satisfactory to good levels, but lower than agreement between p15E and provirus.

Antibody Levels in Field Study Cats

Evaluation of field study cats (FIG. 4) with ROC analyses using provirus as gold standard revealed a good course for antigen p15E, which is in striking contrast to the other antigens.

Because the field study values were generally increased, new cutoff points for this datasets had to be determined. Eight cats were excluded from this study that were besides being provirus positive also immunized (Table 1). The optimal cutoffs were defined as specificity 80% and sensitivity x specificity as maximum (FIG. 5) which was calculated to be OD=0.163 for p15E, resulting in a sensitivity of 77.1% and a specificity of 85.6% (specificity≥80%). FL-74 displayed with a cutoff of 0.647 a sensitivity of 42.9% and a specificity of 80.1%, p45 with a cutoff of 0.531 a sensitivity of 40% and specificity of 81.1%, and EPK211 had a sensitivity of 17.1% and a specificity of 84.6% with a cutoff of 2.411.

Cohen's κ values (specificity of ≥80%) revealed lower levels compared to κ-values of experimentally infected cats, consistent with the differences between the two sets of data evaluated with ROC analyses. The best agreement level was achieved by p15E plotted against provirus (κ=0.55) (FIG. 6). In marked contrast, the other pairs of antigens and pairs of provirus and antigens reached levels of only 0.08 to 0.42 and thus were clearly unsatisfactory. These results indicated that the agreement between p15E and provirus is much better than any combination of p15E with the other antigens.

The fact that the diagnostic sensitivity and specificity of the results of p15(E)-serology versus those of provirus was lower in field cats than in experimentally infected cats can be explained by the observation that exposure to low levels of FeLV may induce seroconversion in absence of proviral DNA in the blood as described by Major et al (2010). Experimental infection is always performed by injection using relatively high loads of FeLV challenge virus, resulting in provirus-positivity and seroconversion. In contrast, infection by FeLV in the field must be highly variable in that cats are exposed to varying infectious pressure resulting in seroconversion in presence of low viral loads. The seemingly lower diagnostic specificity of p15(E) serology in field cats therefore correctly reflects seroconversion to p15(E) in absence of provirus in the blood.

Experimentally Vaccinated Cats

To look at the reactions of vaccinated animals, sera from young, 8 weeks old SPF cats were tested at the beginning of the vaccine study prior to the vaccinations, and again after two times of vaccination, before challenge infection.

Results are summarized in a boxplot (FIG. 7). Results for p45 revealed that of all 65 cats (without Placebo), 56.92% exceeded the cutoff, but 100% were above the cutoff when immunized with LEUCOGEN® FeLV vaccine, as expected. Whole FeLV antigen (FL-74) showed an overall increase in antibody responses (90.77% exceeded the cutoff; 100% when LEUCOGEN® FeLV vaccine vaccinated). In contrast, use of EPK21 1 as antigen for detection of antibodies revealed that 58.46% were above the cutoff, 40% of the cats being vaccinated with LEUCOGEN® FeLV vaccine. With recombinant p15E, 44.62% of cats exceeded the cutoff, and 13.3% of LEUCOGEN® FeLV vaccine vaccinated animals.

Vaccinated Cats from the Field Study

Of all provirus negative cats, 50 cats were vaccinated (Table 1). Eight cats were excluded from this study as besides being immunized they were also provirus positive or even viremic (Table 1). 98% of all animals considered for the study received LEUCOGEN® FeLV vaccine, mostly applied in combination with FELIGEN® feline panleukopenia and feline rhinotracheitis/cat flu vaccine (Virbac Schweiz AG, Glattbrugg, Switzerland; against feline panleukopenia and feline rhinotracheitis/cat flu). Results (FIG. 8) revealed that the antibody reaction was clearly increased using antigens p45 (70%), whole virus (42%), and EPK21 1 (24%). p15E showed a low reactivity to LEUCOGEN® FeLV vaccine vaccinated cats and exceed in the cutoff point in 16% of cases.

We claim:

1. A method for the detection of past or present FeLV infection in a patient, comprising:
   contacting a sample obtained from said patient with an isolated recombinant transmembrane p15E protein consisting of an amino acid sequence set forth as SEQ ID NO: 1, wherein the recombinant transmembrane p15E protein is produced in and isolated from a prokaryote, and wherein the isolated recombinant transmembrane p15E protein forms a binding pair with p15E-specific antibodies, and
   detecting the binding pair,
   wherein detection of the binding pair indicates the past or present FeLV infection in the patient.

2. The method of claim 1, further comprising the step of detecting the presence of FeLV p27 protein in the sample.

3. The method according to claim 2, wherein
   (a) formation of the binding pair between the isolated recombinant transmembrane p15E protein and p15E-specific antibodies in the sample, and the presence of said p27 protein in said sample indicates FeLV viremia and wherein
   (b) formation of the binding pair between the isolated recombinant transmembrane p15E protein and p15E-specific antibodies in the sample, and an absence of said p27 protein in said sample indicates immunity to FeLV.

4. The method of claim 1, further comprising the step of detecting the presence of antibodies against FeLV p45 protein in the sample.

5. The method of claim 1, wherein the prokaryote is *E. coli*.

6. A method, comprising:
   obtaining a sample from a patient
   contacting the sample with an isolated recombinant transmembrane p15E protein consisting of an amino acid sequence set forth as SEQ ID NO: 1, wherein the isolated recombinant transmembrane p15E protein is produced in and isolated from a prokaryote, whereby a binding pair is formed between the isolated recombinant transmembrane p15E protein and p15E-specific antibodies; and
   detecting the binding pair.

7. The method of claim 1, wherein the past or present FeLV infection is detected at a diagnostic sensitivity of at least 95%.

8. The method of claim 6, wherein the past or present FeLV infection is detected at a diagnostic sensitivity of at least 95%.

9. The method of claim 1, wherein detection of the binding pair indicates a present FeLV infection in the patient.

10. The method of claim 6, wherein detection of the binding pair indicates a present FeLV infection in the patient.

* * * * *

SEQUENCE LISTING

```
<160> NUMBER OF SEQ ID NOS: 1

<210> SEQ ID NO 1
<211> LENGTH: 197
<212> TYPE: PRT
<213> ORGANISM: FeLV A

<400> SEQUENCE: 1

Glu Pro Ile Ser Leu Thr Val Ala Leu Met Leu Gly Gly Leu Thr Val
1               5                   10                  15

Gly Gly Ile Ala Ala Gly Val Gly Thr Gly Thr Lys Ala Leu Leu Glu
            20                  25                  30

Thr Ala Gln Phe Arg Gln Leu Gln Met Ala Met His Thr Asp Ile Gln
        35                  40                  45

Ala Leu Glu Glu Ser Ile Ser Ala Leu Glu Lys Ser Leu Thr Ser Leu
    50                  55                  60

Ser Glu Val Val Leu Gln Asn Arg Arg Gly Leu Asp Ile Leu Phe Leu
65                  70                  75                  80

Gln Glu Gly Gly Leu Cys Ala Ala Leu Lys Glu Glu Cys Cys Phe Tyr
                85                  90                  95

Ala Asp His Thr Gly Leu Val Arg Asp Asn Met Ala Lys Leu Arg Glu
            100                 105                 110

Arg Leu Lys Gln Arg Gln Leu Phe Asp Ser Gln Gln Gly Trp Phe
        115                 120                 125

Glu Gly Trp Phe Asn Arg Ser Pro Trp Phe Thr Thr Leu Ile Ser Ser
    130                 135                 140

Ile Met Gly Pro Leu Leu Ile Leu Leu Leu Ile Leu Leu Phe Gly Pro
145                 150                 155                 160
```

-continued

```
Cys Ile Leu Asn Arg Leu Val Gln Phe Val Lys Asp Arg Ile Ser Val
                165                 170                 175
Val Gln Ala Leu Ile Leu Thr Gln Gln Tyr Gln Gln Ile Lys Gln Tyr
            180                 185                 190
Asp Pro Asp Arg Pro
            195
```